United States Patent
Hagemeyer et al.

(10) Patent No.: US 9,555,397 B2
(45) Date of Patent: Jan. 31, 2017

(54) PRE-GOLD-PLATING PD-AU-COATED SHELL CATALYSTS

(71) Applicant: CLARIANT PRODUKTE (DEUTSCHLAND) GMBH, Frankfurt am Main (DE)

(72) Inventors: Alfred Hagemeyer, Sunnyvale, CA (US); Carolin Fischer, Rosenheim (DE); Gerhard Mestl, Munich (DE); Peter Scheck, Gilching (DE); Roman Bobka, Munich (DE)

(73) Assignee: CLARIANT PRODUKTE (DEUTSCHLAND) GMBH, Frankfurt am Main (DE)

( * ) Notice: Subject to any disclaimer, the term of this patent is extended or adjusted under 35 U.S.C. 154(b) by 73 days.

(21) Appl. No.: 14/379,266

(22) PCT Filed: Feb. 20, 2013

(86) PCT No.: PCT/EP2013/053334
§ 371 (c)(1),
(2) Date: Aug. 15, 2014

(87) PCT Pub. No.: WO2013/142293
PCT Pub. Date: Aug. 29, 2013

(65) Prior Publication Data
US 2015/0011386 A1    Jan. 8, 2015

(30) Foreign Application Priority Data
Feb. 20, 2012    (DE) .................. 10 2012 003 236

(51) Int. Cl.
*B01J 23/58*    (2006.01)
*B01J 23/52*    (2006.01)
(Continued)

(52) U.S. Cl.
CPC ............... *B01J 23/52* (2013.01); *B01J 23/66* (2013.01); *B01J 35/008* (2013.01);
(Continued)

(58) Field of Classification Search
CPC ......... B01J 37/0201; B01J 23/58; B01J 37/18; B01J 35/008; B01J 37/16; B01J 37/0221; B01J 23/52; B01J 37/0228; B01J 23/66; C07C 67/055
(Continued)

(56) References Cited

U.S. PATENT DOCUMENTS 5,066,365 A    11/1991    Roscher et al.
5,691,267 A    11/1997    Nicolau et al.
(Continued)

FOREIGN PATENT DOCUMENTS

DE    196 27 844    12/1999
DE    10 2005 061 382    6/2007
(Continued)

OTHER PUBLICATIONS

PCT international Search Report for PCT/EP2013/053334, mailed May 22, 2013.
(Continued)

*Primary Examiner* — Colleen Dunn
*Assistant Examiner* — Haytham Soliman
(74) *Attorney, Agent, or Firm* — Anthony A. Bisulca

(57) ABSTRACT

The present invention relates to a method for producing a shell catalyst that is suitable for producing vinyl acetate monomer (VAM). The present invention also relates to a shell catalyst that can be obtained by the method according to the invention as well as the use of the shell catalyst according to the invention for producing VAM.

19 Claims, 1 Drawing Sheet

(51) Int. Cl.
*B01J 37/02* (2006.01)
*B01J 37/16* (2006.01)
*B01J 37/18* (2006.01)
*B01J 23/66* (2006.01)
*B01J 35/00* (2006.01)
*C07C 67/055* (2006.01)

(52) U.S. Cl.
CPC ....... *B01J 37/0201* (2013.01); *B01J 37/0221* (2013.01); *B01J 37/0228* (2013.01); *B01J 37/16* (2013.01); *B01J 37/18* (2013.01); *C07C 67/055* (2013.01); *B01J 23/58* (2013.01); *Y02P 20/582* (2015.11)

(58) Field of Classification Search
USPC .......................................................... 503/330
See application file for complete search history.

(56) References Cited

U.S. PATENT DOCUMENTS

| | | | |
|---|---|---|---|
| 5,693,586 | A | 12/1997 | Nicolau et al. |
| 6,015,769 | A | 1/2000 | Wang |
| 8,466,082 | B2 | 6/2013 | Hagemeyer et al. |
| 8,586,780 | B2 | 11/2013 | Hagemeyer et al. |
| 8,927,452 | B2 | 1/2015 | Hagemeyer et al. |
| 2001/0048970 | A1 | 12/2001 | Hagemeyer et al. |
| 2009/0291845 | A1 | 11/2009 | Neto et al. |
| 2010/0185010 | A1 | 7/2010 | Hagemeyer et al. |
| 2010/0190638 | A1 | 7/2010 | Hagemeyer et al. |
| 2010/0197488 | A1* | 8/2010 | Hagemeyer ................ B01J 2/16 502/242 |
| 2010/0197956 | A1 | 8/2010 | Hagemeyer et al. |
| 2011/0319655 | A1 | 12/2011 | Hagemeyer et al. |
| 2012/0289737 | A1 | 11/2012 | Hagemeyer et al. |
| 2013/0172603 | A1 | 7/2013 | Hagemeyer et al. |
| 2014/0081041 | A1 | 3/2014 | Bobka et al. |
| 2015/0031911 | A1 | 1/2015 | Mestl et al. |
| 2015/0126360 | A1 | 5/2015 | Mestl et al. |
| 2015/0126361 | A1 | 5/2015 | Mestl et al. |

FOREIGN PATENT DOCUMENTS

| | | |
|---|---|---|
| DE | 10 2007 025 317 | 12/2008 |
| DE | 10 2007 025 442 | 12/2008 |
| DE | 10 2007 025 356 | 1/2009 |
| DE | 10 2008 032 080 | 1/2010 |
| DE | 10 2010 026 462 | 1/2012 |
| WO | WO 99/62632 | 12/1999 |
| WO | WO 2008/145395 | 12/2008 |

OTHER PUBLICATIONS

PCT International Preliminary Report on Patentability for PCT/EP2013/053334, mailed Aug. 26, 2014.
DE 10 2007 025 317 Machine English Translation, Dec. 4, 2008.
DE 10 2008 032 080 English Abstract, Jan. 12, 2012.

* cited by examiner

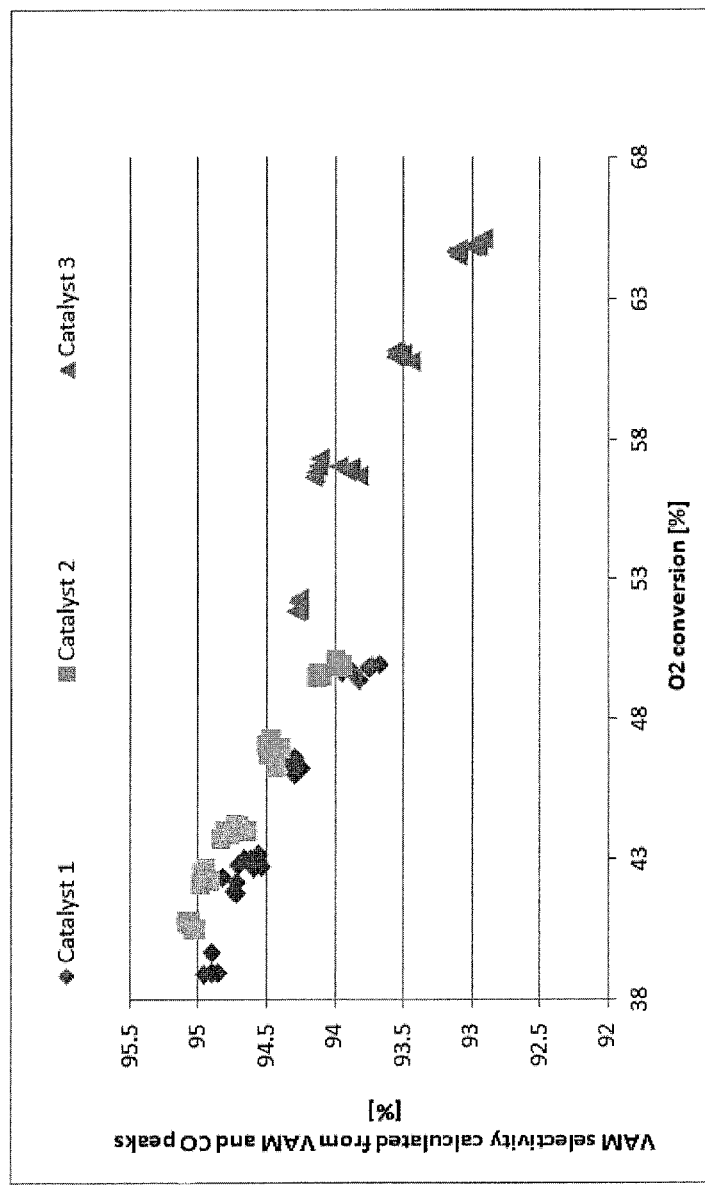

PRE-GOLD-PLATING PD-AU-COATED SHELL CATALYSTS

The present invention relates to a novel method for producing a shell catalyst which is suitable for producing vinyl acetate monomer (VAM). The present invention also relates to a shell catalyst which can be obtained by the method according to the invention as well as the use of the shell catalyst according to the invention for producing VAM.

Supported catalysts which contain palladium and gold have already been known for some time. VAM is usually produced in the presence of catalysts containing palladium and gold from a reaction mixture of ethylene, oxygen and acetic acid. Various production methods for such supported catalysts are already known. Thus, for example, precursor compounds which contain the corresponding metals are applied, dissolved preferably in an aqueous solution, to the surface of a support body. The support body containing the corresponding precursor compounds is then usually calcined under oxidic conditions in a high-temperature oven, wherein the metal-containing precursor compounds are converted into the metal oxides. The support bodies which contain the corresponding metal oxides are then subjected to reduction to the elemental metals.

Vinyl acetate monomer is an important component in the production of polyvinyl acetate, vinyl acetate copolymers (such as ethylene vinyl acetates or ethylene vinyl alcohol copolymers) and polyvinyl alcohol. Because of the wide field of use of these polymers, for example as binders in the construction, paints, and varnishes sectors and as raw material for the adhesive, paper- and textile industries, there is still a high requirement for VAM and for constant improvement of the activity and selectivity of catalysts for their production.

Normally, in the synthesis of VAM, shell catalysts are used in which elemental Pd and Au are situated in an outer shell of a catalyst support body. To produce them, a mixed solution of a Pd-containing precursor compound and an Au-containing precursor compound is normally applied to a catalyst support body which is then dried, and the metal components of the precursor compounds are converted into the elemental metals. The Pd/Au combination normally leads to a good selectivity or activity of the catalyst. Due to the capital intensity of corresponding VAM production plants and increasingly high raw material costs, in particular for ethylene, there is however a constant requirement to optimize the economic efficiency of the method for producing VAM by means of improved catalysts.

The object of the present invention was therefore to provide a method for producing a shell catalyst which results in shell catalysts that are superior to previous catalysts as regards activity and selectivity in the synthesis of VAM.

This object was achieved by a method according to the invention with which shell catalysts with significantly increased selectivity and activity for VAM can be produced.

The method according to the invention for producing a shell catalyst is characterized by the following method steps:
(a) subjecting a packed bed of a catalyst support body (support body) to a circulating movement;
(b) bringing an atomized, aqueous solution containing an Au-containing precursor compound into contact with the packed bed of the catalyst support body subjected to the circulating movement, by spraying on;
(c) bringing an atomized, aqueous solution containing a Pd-containing precursor compound into contact with the catalyst support body obtained after step (b); and
(d) reducing the metal components of the precursor compounds to the elemental metals by subjecting the catalyst support body obtained in step (c) to a temperature treatment in a non-oxidizing atmosphere.

In step (c) of the method according to the invention, it is also preferred that the solution is brought into contact by being sprayed onto a packed bed of the catalyst support body subjected to a circulating movement.

According to one embodiment of the process according to the invention, no additional precursor compounds of catalytically active metals are used next to AU-precursor compounds, in step (b), in particular no Pd-precursor compounds.

By the term "shell catalyst" is meant a catalyst which comprises a support body and a shell with catalytically active material, wherein the shell can be formed in two different ways:

Firstly, a catalytically active material can be present in the outer area of the support body, with the result that the material of the support body serves as matrix for the catalytically active material and the area of the support body which is impregnated with the catalytically active material forms a shell around the unimpregnated core of the support body. Secondly, an additional layer in which a catalytically active material is present can be applied to the surface of the support body. This layer thus forms an additional material layer which is constructed as a shell around the support body. In the latter variant, the support body material is not a constituent of the shell, but the shell is formed by the catalytically active material itself or a matrix material which comprises a catalytically active material. In an embodiment of the present invention, this is preferably the first-named variant of a shell catalyst.

In the catalyst produced by the method according to the invention, the metals are present either in monoatomic form or in the form of aggregates. However, they are preferably present in the form of aggregates. These monoatomic atoms or aggregates are dispersed predominantly uniformly inside the shell of the shell catalyst. By an aggregate is meant the clustering of several metal atoms to form a composite which lies between monoatomic form and metallic form. The term also includes so-called metal clusters.

The shell thickness of the outer shell of the support body is preferably 1 to 70%, more preferably 2 to 60%, even more preferably 3 to 50% and most preferably 4 to 40% of half of the total thickness of the support body. The named percentage therefore relates to half of the total thickness as, depending on the shape of the support body during production, e.g. by spray impregnation with a solution containing precursor compound, the precursor compound either penetrates the support body material from two outer surfaces (sphere) or, if the support body material has a more complex shape, such as e.g. that of a hollow cylinder, there are an outer surface and an inner surface which the precursor compound penetrates. In the case of support body materials deviating from sphere geometry the total thickness of the support is measured along the longest support body axis. The outer shell boundary is equalized with the outer boundary of the metal-containing support body. By inner shell boundary is meant the boundary, located inside the support body, of the outer metal-containing shell which is at such a distance from the outer shell boundary that 95 wt-% of all of the metal contained in the support body is located in the outer shell. However, the shell thickness is preferably not more than 70%, by preference not more than 60%, more preferably not more than 50%, even more preferably not more than 40% and most preferably not more than 30%, in each case relative to half of the total thickness of the support body.

The metal-impregnated support body preferably contains no more than 5% of the total metal in its inner area, thus inside the area that is delimited to the outside by the inner shell boundary of the metal shell.

With regard to the shell thickness of the catalyst, the maximum concentration of metal preferably lies in the area of the outer shell, particularly preferably at the outer edge of the outer shell, i.e. close to the geometric catalyst surface. The metal concentration preferably decreases towards the inner shell boundary.

The support body preferably consists of an inert material. It can be porous or non-porous. However, the support body is preferably porous. The support body preferably consists of particles with a regular or irregular shape, such as for example spheres, tablets, cylinders, solid cylinders or hollow cylinders, rings, stars or other shapes, and its dimensions, such as e.g. diameter, length or width, are in a range of from 1 to 10 mm, preferably 3 to 9 mm. Spherical, i.e. e.g. sphere-shaped, particles with a diameter of from 3 to 8 mm are preferred according to the invention. However, the support body material can comprise any non-porous and porous substance, preferably porous substance. Examples of materials for this are titanium oxide, silicon oxide, aluminium oxide, zirconium oxide, magnesium oxide, silicon carbide, magnesium silicate, zinc oxide, zeolites, sheet silicates and nanomaterials, such as for example carbon nanotubes or carbon nanofibres, preferably when the support body material itself is a heterogeneous catalyst.

The above-named oxidic support body materials can be used for example in the form of mixed oxides or defined compositions, such as for example $TiO_2$, $SiO_2$, $Al_2O_3$, $ZrO_2$, MgO, SiC or ZnO. Furthermore, soots, ethylene black, charcoal, graphite, hydrotalcites or further support body materials known per se to a person skilled in the art can preferably be used in different possible modifications. The support body materials can preferably be doped for instance with alkali or alkaline earth metals or also with phosphorus, halide and/or sulphate salts. In particular it is preferred if the catalyst support comprises $SiO_2$, preferably in a quantity in the range of from 65 to 98 wt-%, relative to the total weight of the support body. The oxidic support body materials can also have a proportion of zirconium dioxide. The proportion of $ZrO_2$ in these materials is preferably in the range of from 5 to 20 wt-%.

The BET surface area of the support body material without the coating with the precursor compounds is 1 to 1,000 $m^2/g$, preferably 10 to 600 $m^2/g$, particularly preferably 20 to 400 $m^2/g$ and quite particularly preferably between 100 and 200 $m^2/g$. The BET surface area is determined using the 1-point method by absorption of nitrogen in accordance with DIN 66132.

In addition, it can be preferred that the integral pore volume of the support body material (determined in accordance with DIN 66133 (Hg porosimetry)) without the coating with the precursor compound is greater than 0.1 ml/g, preferably greater than 0.18 ml/g and most preferably in the range of from 0.25 to 0.5 ml/g.

The bulk density of the support body preferably lies in the range of from 480 to 650 g/l, more preferably in the range of from 500 to 630 g/l.

The support body is usually produced by subjecting a plurality of support bodies to a "batch" process, in the individual process steps of which the shaped bodies are subject to relatively high mechanical stress for example by using stirring and mixing tools.

In addition, the shell catalyst produced by the method according to the invention can be subjected to a strong mechanical load stress during the filling of a reactor, which can result in an undesired formation of dust as well as damage to the support body, in particular to its catalytically active shell located in an outer area.

In particular, to keep the wear of the catalyst produced by the method according to the invention within reasonable limits, the shell catalyst has a hardness greater than/equal to 20 N, preferably greater than/equal to 25 N, further preferably greater than/equal to 35 N and even more preferably greater than/equal to 40 N, particularly preferably in the range of from 40 to 65 N. The hardness is ascertained by means of an 8M tablet-hardness testing machine from Dr Schleuniger Pharmatron AG, determining the average for 99 shell catalysts, after drying of the catalyst at 130° C. for two hours, wherein the apparatus settings are as follows:

Distance from the shaped body: 5.00 mm
Time delay: 0.80 s
Feed type: 6 D
Speed: 0.60 mm per second The hardness of the catalyst produced by the method according to the invention can be influenced for example by means of variations in certain parameters of the method for producing the support body, for example by the calcining time and/or the calcining temperature of the support body. The just-mentioned calcining is not a calcining of the support body impregnated with the metal-containing precursor compounds, but merely a calcining step for producing the support body before the precursor compounds are applied.

It is also preferred that 80% of the integral pore volume of the support body is formed by mesopores and macropores, preferably at least 85% and most preferably at least 90%. This counteracts a reduced activity, effected by diffusion limitation, of the catalyst produced by the method according to the invention, in particular in the case of metal-containing shells with relatively large thicknesses. By the terms micropores, mesopores and macropores are meant in this case pores which have a diameter of less than 2 nm, a diameter of from 2 to 50 nm and a diameter of more than 50 nm respectively.

The activity of the shell catalyst produced by the method according to the invention normally depends on the quantity of the metal loading in the shell: As a rule, the more metal there is in the shell, the higher the activity. The thickness of the shell here has a small influence on the activity, but is a decisive variable with respect to the selectivity of the catalysts. With equal metal loading of the catalyst support, the smaller the thickness of the outer shell of the catalyst is, the higher the selectivity of the shell catalysts produced by the method according to the invention is in general. It is thus decisive to set an optimum ratio of metal loading to shell thickness in order to guarantee the highest possible selectivity with the highest possible activity. According to a further preferred embodiment of the catalyst produced by the method according to the invention, the shell of the catalyst therefore has a thickness in the range of from 5 μm to 2000 μm, preferably from 10 μm to 1500 μm, more preferably from 15 to 1000 μm. If the shell catalyst is to be used for example as catalyst for the synthesis of vinyl acetate, its shell thickness preferably lies in the range of from 10 μm to 400 μm, more preferably in the range of from 15 μm to 300 μm.

The thickness of the shell can be measured visually by means of a microscope. The area in which the metal is deposited appears black, while the areas free of noble metals appear white. As a rule, the boundary between areas containing noble metals and areas free of them is very sharp and can be clearly recognized visually. If the above-named boundary is not sharply defined and accordingly not clearly recognizable visually, the thickness of the shell corresponds—as already mentioned—to the thickness of a shell, measured starting from the outer surface of the catalyst support, which contains 95% of the noble metal deposited on the support.

In order to ensure a largely uniform activity of the catalyst produced by the method according to the invention over the thickness of the noble metal-containing shell, the noble-metal concentration should vary only relatively little over the shell thickness. It is therefore preferred if, over an area of 90% of the shell thickness, wherein the area is at a distance of 5% of the shell thickness from each of the outer and inner shell limits, the profile of the noble-metal concentration of the catalyst varies from the average noble-metal concentration of this area by a maximum of +/−20%, preferably by a maximum of +/−15% and by preference by a maximum of +/−10%. Such profiles can be obtained by bringing an atomized, aqueous solution containing the precursor compound(s) into contact, as described further below, with a packed bed of a catalyst support body subjected to a circulating movement, by spraying on. In order to achieve the circulating movement of the packed bed of the support bodies, it is in particular suitable to introduce the packed bed of the supports into a fluidized bed, a fluid bed or an Innojet-Aircoater as described further below. The just-mentioned distribution of the metal loading preferably describes a rectangular function. In addition to the rectangular function, the metal loading inside the shell can however also describe a triangular or trapezium function in the case of which the metal concentration gradually decreases from the outside to the inside in the shell. It is therefore preferred according to the invention that any application of precursor compounds mentioned in this application is carried out as mentioned above.

It is also possible in the method according to the invention that during step (c), i.e. the spraying on (coating) of the Pd-containing precursor compound, a mixed solution of a Pd-containing precursor compound and an Au-containing precursor compound is also sprayed on, i.e. the solution sprayed on in step (c) can additionally also contain an Au-containing precursor compound. Alternatively to this, during the spraying on of the Pd-containing precursor compound from a solution, it is also possible to additionally spray on an Au-containing precursor compound from a separate solution. If an Au-containing precursor compound is also sprayed on during step (c), it is preferred that the latter is applied from a separate solution from the Pd-containing precursor compound, in particular because the spraying on of the Au-containing precursor compound of step (b) can thus be continued during step (c), the spraying on of the Pd-containing precursor compound. In other words, preferably only one solution containing an Au-containing precursor compound is sprayed on first. After a specified spraying-on time of the Au-containing precursor compound, a solution containing a Pd-containing precursor compound is preferably additionally sprayed on. The spraying on of the Au-containing precursor compound can be continued until the end of the spraying on of the Pd-containing precursor compound, but it can also finish before the end of the spraying on of the Pd-containing precursor compound.

Furthermore it is preferred that after step (c) a solution containing an Au-containing precursor compound is furthermore sprayed onto the support body. This optional step is called step (c1) in this application and is preferably carried out before step (d).

The method according to the invention can consequently be carried out in the following variants: step (b): spraying on of the solution containing the Au-containing precursor compound; step (c): spraying on of the solution containing the Pd-containing precursor compound; the spraying on of an Au-containing precursor compound can optionally also take place during step (c), or the spraying on of the solution containing the Au-containing precursor compound can be completely or partially continued during step (c); optional step (c1): a solution containing an Au-containing precursor compound can furthermore be sprayed on here; step (c1) can be carried out independently of whether an Au-containing precursor compound is additionally sprayed on in step (c). However, if in step (c) an Au-containing precursor compound is likewise sprayed on all the time, it is preferred that the spraying on of the Au-containing precursor compound is simply continued without interruption in step (c1). However, in step (c1), preferably only an Au-containing precursor compound, and no Pd-containing precursor compound, is sprayed on.

Irrespective of which of the named method variants is selected, for obtaining a shell catalyst with increased selectivity and activity it is primarily decisive that the spraying on of the Au-containing precursor compound is carried out before the spraying on of the Pd-containing precursor compound. This means that, during step (a) of the spraying on of the solution containing the Au-containing precursor compound, no additional spraying on of a Pd-containing precursor compound takes place. However, this does not rule out the possibility that, during the step of the spraying on of a solution containing the Pd-containing precursor compound, an Au-containing precursor compound is also sprayed on.

The spraying of the precursor compounds in steps (b) and (c) of the method according to the invention onto the support body can be carried out by methods known per se.

In the state of the art, the application of a solution containing the precursor compounds often takes place by steeping, by immersing the support body in the precursor compound solutions or according to the incipient wetness method. However, it is difficult to produce a shell catalyst with a defined shell and a homogeneous metal distribution using these steeping methods.

The spraying on of the precursor compounds in steps (b) and (c) and optional step (c1) in the method according to the invention is preferably carried out by spraying the support body with an aqueous solution containing the precursor compound. Here, a packed bed of the support body is subjected to a circulating movement, so that the support body can be uniformly sprayed from all sides. The circulating movement can in principle be carried out by any known mechanical stirring device such as, for example, a coating drum. It is however particularly preferred according to the invention that the circulating movement of the support bodies is carried out with the help of a process gas, e.g. in a fluid bed, a fluidized bed or in a coating chamber of an Innojet-Aircoater. At the same time, the support bodies are moved by the process gas being blown in. Here the process gas is preferably controlled so that the support bodies are held in a controlled glide layer of the process gas. Here the process gas is preferably heated so that the solvent rapidly evaporates. In this way, the precursor compounds are present in the named defined shell of the support body. The spraying rate is preferably chosen during the spraying on such that a balance is achieved between the evaporation rate of the solvent and the feed rate of the precursor compounds on the support body. This makes it possible to set the desired shell thickness and palladium/gold distribution in the shell. Depending on the spraying rate, the shell thickness can thus be infinitely variably set and optimized, for example up to a thickness of 2 mm. But very thin shells with a thickness of less than 1000 μm are thus also possible.

It is particularly preferred that the spraying rate is constant during spraying on in all conceivable steps of the application of precursor compounds and lies in the range of a mass flow of the solution containing the precursor compound(s) of from 0.5 to 10 g/min per 100 g of support shaped body to be coated, more preferably in the range of from 1 to 8 g/min per 100 g of support body to be coated, even more preferably 2 to 6 g/min per 100 g of support body to be coated and most preferably 3.5 to 5 g/min of support body to be coated. In other words the ratio of the weight of the sprayed-on solution to the weight of the packed bed of the support body lies in the range of from 0.005 to 0.1, more preferably 0.01 to 0.08, even more preferably 0.02 to 0.06 and most preferably 0.035 to 0.05. A mass flow or ratio above the range indicated leads to catalysts with lower selectivity, a mass flow or ratio below the range indicated has no marked negative effects on the catalyst performance, but the catalyst production is very time-consuming and the production is thus inefficient.

Starting from a constant spraying rate during the application of all solutions, it is preferred if the ratio of the time of application of the solution in step (b) to the time of application of the solution in step (c) lies in the range of from 5:1 to 1:5, preferably 4:1 to 1:2, more preferably 3:1 to 1:1 and most preferably 2.5:1 to 1.5:1.

If a fluid bed unit is used, it is preferred if the support bodies circulate elliptically or toroidally in the fluid bed. To give an idea of how the support bodies move in such fluid beds, it may be stated that in the case of "elliptical circulation" the support bodies move in the fluid bed in a vertical plane on an elliptical path, the size of the main and secondary axes changing. In the case of "toroidal" circulation the support bodies move in the fluid bed in a vertical plane on an elliptical path, the size of the main and secondary axes changing, and in a horizontal plane on a circular path, the size of the radius changing. On average, the support bodies move in a vertical plane on an elliptical path in the case of an "elliptical circulation", on a toroidal path in the case of a "toroidal circulation", i.e. a support body travels helically over the surface of a torus with a vertically elliptical section.

The spraying of the precursor compounds onto the support body in steps (b) and (c) and optional step (c1) of the method according to the invention is particularly preferably carried out by means of a fluid bed in a fluid bed unit. It is particularly preferred that there is a so-called controlled glide layer of process gas in the unit. For one thing, the support bodies are thoroughly mixed by the controlled glide layer of process gas, wherein they simultaneously rotate about their own axis, and are dried evenly by the process gas. For another, the support bodies pass through the spraying process (application of the precursor compounds) at a virtually constant frequency because of the consistent orbital movement of the support bodies brought about by the controlled glide layer of process gas. A largely uniform shell thickness, or penetration depth of the noble metals into the support body, of a treated phase of support bodies is thereby achieved. A further result is that the noble-metal concentration varies only relatively slightly over a relatively large area of the shell thickness, i.e. the noble-metal concentration describes an approximately rectangular function over a large area of the shell thickness, whereby a largely uniform activity of the resulting catalyst is guaranteed over the thickness of the noble metal shell. However, in this way it is also possible to set the noble-metal concentration in the shell so that this describes a triangular or trapezium function.

Suitable conventional coating drums, fluidized bed units or fluid bed units for carrying out the spraying on of the precursor compounds in the method according to the invention are known in the state of the art and are sold for example by companies such as Heinrich Brucks GmbH (Alfeld, Germany), ERWEKA GmbH (Heusenstamm, Germany), Stechel (Germany), DRIAM Anlagenbau GmbH (Eriskirch, Germany), Glatt GmbH (Binzen, Germany), D.S. Divisione Verniciatura (Osteria, Italy), HOFER-Pharma Maschinen GmbH (Weil am Rhein, Germany), L. B. Bohle Maschinen and Verfahren GmbH (Enningerloh, Germany), Lödige Maschinenbau GmbH (Paderborn, Germany), Manesty (Merseyside, Great Britain), Vector Corporation (Marion (Iowa) USA), Aeromatic-Fielder AG (Bubendorf, Switzerland), GEA Process Engineering (Hampshire, Great Britain), Fluid Air Inc. (Aurora, Ill., USA), Heinen Systems GmbH (Varel, Germany), Hüttlin GmbH (Steinen, Germany), Umang Pharmatech Pvt. Ltd. (Maharashtra, India) and Innojet Technologies (Lörrach, Germany). Particularly preferred fluid bed equipment is sold with the name Innojet® Air-Coater or Innojet® Ventilus by Innojet Technologies. Here the IAC-5 coater, the IAC-150 coater or the IAC-025 coater, all from the company Innojet, is particularly preferably used.

Furthermore the support body used in the method according to the invention is heated during the spraying on of the solutions containing the precursor compounds in steps (b) and (c) and optional step (c1), for example by means of heated process gas. The process gas here preferably has a temperature of from 10 to 110° C., more preferably 40 to 100° C. and most preferably 50 to 90° C. The named upper limits should be adhered to in order to guarantee that the named outer shell has a small layer thickness with a high concentration of noble metal.

Air is preferably used as process gas, but inert gases such as for example nitrogen, $CO_2$, helium, neon, argon or mixtures thereof can also be used.

As already mentioned further above, the spraying (coating) of the precursor compounds onto the catalyst support body in steps (b) and (c) and optional step (c1) is preferably carried out by application from aqueous solutions. Water and mixtures of water and solvents, however preferably deionized water, are suitable as solvents for the transition metal-precursor compounds in which the selected metal compound(s) is/are soluble and which, after application to the catalyst support, can be easily removed again from same by drying. Preferred solvents are unsubstituted carboxylic acids, in particular acetic acid and ketones, such as acetone.

The spraying on of the solutions containing the precursor compounds is effected in all the method steps of the method according to the invention preferably by atomizing the solution with the help of a spraying nozzle. Here, an annular gap nozzle is preferably used which sprays a spray cloud the plane of symmetry of which preferably runs parallel to the plane of the device base. Due to the 360° circumference of the spray cloud, the shaped bodies falling centrally can be sprayed particularly evenly with the solution. The annular gap nozzle, i.e. its orifice, is preferably completely embedded in the apparatus carrying out the circulating movement of the support bodies.

According to a further preferred embodiment of the method according to the invention, it is provided that the annular gap nozzle is centrally arranged in the base of the apparatus carrying out the circulating movement of the support bodies and the mouth of the annular gap nozzle is completely embedded in the apparatus. It is thereby guaranteed that the free path of the drops of the spray cloud until they meet a shaped body is relatively short and, accordingly, relatively little time remains for the drops to coalesce into larger drops, which could work against the formation of a largely uniform shell thickness.

The atomization of the solutions preferably takes place in the method according to the invention in such a way that the solutions meet the support bodies in the form of an aerosol. The size of the droplets when they meet the support bodies preferably lies here in the range of from 1 to 100 μm, preferably from 10 to 40 μm. It was found that too small a droplet size leads to catalysts which display a poor activity, whereas too large a droplet size leads to catalysts with a poor VAM selectivity.

The solutions containing the Au-containing precursor compound used in step (b) and optional step (c1) contain Au preferably in the range of from 0.01 to 10 wt-%, more preferably 0.1 to 8 wt-%, even more preferably 0.2 to 5 wt-% and most preferably 0.3 to 2 wt-%, relative to the atomic weight proportion of the metal in solution. The same also applies to a solution which contains the Au-containing precursor compound, which is applied at the same time as the solution used in step (c).

The solution containing the Pd-containing precursor compound used in step (c) contains Pd preferably in the range of from 0.1 to 10 wt-%, more preferably 0.5 to 7 wt-%, even more preferably 0.7 to 5 wt-% and most preferably 1 to 2.5 wt-%, relative to the atomic weight proportion of the metal in solution.

If in step (c) a solution is used which, in addition to the Pd-containing precursor compound, also comprises an Au-containing precursor compound, this solution preferably contains the same proportions of Pd and Au as indicated for the individual solutions.

If the metal contents of the above-mentioned solutions are above the ranges indicated, shell catalysts which have a lower selectivity result. Metal contents below the ranges indicated have a negative effect on the activity of the catalysts obtained and lead to significantly longer spraying-on times with a corresponding adverse effect on the profitability of the method.

It is possible that the spraying of the precursor compounds onto the support body in step (b) is followed by a drying step before the Pd-containing precursor compound is sprayed on in step (c). The same also applies optionally if step (c1) is carried out after step (c). The drying step is preferably carried out below the decomposition temperature of the precursor compounds, in particular at the temperatures mentioned further above. By a decomposition temperature is meant the temperature at which the precursor compounds start to decompose. The drying preferably takes place either by the process air in the fluid bed or the fluidized bed, by standing in air or in a drying oven, preferably at a temperature in the range of from 60° C. to 120° C. It is however furthermore particularly preferred that steps (b), (c) and optionally (c1) follow each other directly, with the result that no drying step is carried out between them. This takes place in that, immediately after the spraying on of the solution containing the precursor compound in step (b), the solution containing the Pd-containing precursor compound from step (c), or immediately after step (c), the solution containing the Au-containing precursor compound from optional step (c1) is sprayed on.

In addition a step of intermediate calcining for oxidizing the precursor compound to the metal oxides can optionally be carried out between the spraying on of the solutions in steps (b) and (c) (and optionally (c1)). Likewise a step of intermediate reduction for reducing the precursor compounds to the metals can optionally be carried out. However, it is particularly preferred that neither a drying, nor a calcining, nor a reducing step takes place between the steps of spraying on the two precursor compounds in steps (b), (c) and optionally (c1).

After step (b) the catalyst support body preferably contains a proportion of Au in the range of from 0.05 to 0.2 wt-%, more preferably in the range of from 0.09 to 0.16 wt-%, relative to the total weight of the catalyst support body after drying (i.e. relative to the anhydrous catalyst precursor).

After step (c) the catalyst support body preferably contains a proportion of Pd in the range of from 0.6 to 2 wt-%, more preferably in the range of from 0.7 to 1.6 wt-%, relative to the total weight of the catalyst support body after drying. After step (c) the catalyst support body preferably contains a proportion of Au in the range of from 0.1 to 1 wt-%, more preferably in the range of from 0.3 to 0.6 wt-%, relative to the total weight of the catalyst support body after drying.

The Au-containing precursor compound and Pd-containing precursor compound in steps (b), (c) and optionally (c1) is preferably a water-soluble compound.

The Pd-containing precursor compound is preferably selected from: nitrate compounds, nitrite compounds, acetate compounds, tetraammine compounds, diammine compounds, hydrogen carbonate compounds and hydroxidic metallate compounds.

Examples of preferred Pd-containing precursor compounds are water-soluble Pd salts. According to a particularly preferred embodiment of the method according to the invention, the Pd precursor compound is selected from the group consisting of $Pd(NH_3)_4(HCO_3)_2$, $Pd(NH_3)_4(HPO_4)$, ammonium Pd oxalate, Pd oxalate, $K_2Pd(oxalate)_2$, Pd(II) trifluoroacetate, $Pd(NH_3)_4(OH)_2$, $Pd(NO_3)_2$, $H_2Pd(OAc)_2(OH)_2$, $Pd(NH_3)_2(NO_2)_2$, $Pd(NH_3)4(NO_3)_2$, $H_2Pd(NO_2)_4$, $Na_2Pd(NO_2)_4$, $Pd(OAc)_2$ as well as freshly precipitated $Pd(OH)_2$. The production of freshly precipitated $Pd(OH)_2$ is preferably carried out as follows: A 0.1 to 40 wt-% aqueous solution is preferably produced from tetrachloropalladate. A base, preferably an aqueous solution of potassium hydroxide, is then added to this solution until a brown solid, namely $Pd(OH)_2$ precipitates. To produce a solution for application to the catalyst support, the freshly precipitated $Pd(OH)_2$ is isolated, washed and dissolved in an aqueous alkaline solution. Dissolution preferably takes place at a temperature within the range of from 4 to 40° C., particularly preferably 15 to 25° C. A lower temperature is not possible because of the freezing point of water, a higher temperature brings with it the disadvantage that after a certain time $Pd(OH)_2$ precipitates again in the aqueous solution and does not dissolve.

Furthermore the Pd-nitrite precursor compounds can also be used in the method according to the invention. Preferred Pd nitrite precursor compounds are for example those which are obtained by dissolving $Pd(OAc)_2$ in an $NaNO_2$ or $KNO_2$ solution.

The Au-containing precursor compounds in steps (b) and (c) and optional step (c1) are preferably selected in each case independently of each other from: acetate compounds, nitrite or nitrate compounds and hydroxidic metallate compounds.

Examples of preferred Au-containing precursor compounds are water-soluble Au salts. According to a particularly preferred embodiment of the method according to the invention, the Au precursor compound is selected from the group consisting of $KAuO_2$, $NaAuO_2$, $LiAuO_2$, $RbAuO_2$, $Ba(AuO_2)_2$, $NaAu(OAc)_3(OH)$, $KAu(NO_2)_4$, $KAu(OAc)_3(OH)$, $LiAu(OAc)_3(OH)$, $RbAu(OAc)_3(OH)$, $HAu(NO_3)_4$ and $Au(OAc)_3$. It may be advisable to add the $Au(OAc)_3$ or the $KAuO_2$ in each case freshly by precipitating the oxide, hydroxide from an auric acid solution, washing and isolating the precipitate as well as taking up same in acetic acid or KOH respectively. Potassium aurate is particularly preferably used as Au-containing precursor compound, which is used in dissolved form for application to the support body. The production of a potassium aurate solution is known in the literature and can be produced in accordance with the production methods disclosed in the documents WO 99/62632 and U.S. Pat. No. 6,015,769. Particularly preferably the Au-containing precursor compounds in steps (b) and (c) and optional step (c1) are the same, in particular $KAuO_2$.

The named precursor compounds are cited only by way of example and any other precursor compounds can be used. It is particularly preferred that the precursor compounds are substantially chloride-free. By substantially chloride-free is meant that the empirical formula of the compound comprises no chloride, but it is not ruled out that the compound contains unavoidable chloride impurities for example due to production conditions. It is particularly preferred here that the maximum chloride content in a solution containing the Au-precursor compound does not exceed 5000 ppm, more preferably 3000 ppm and most preferably 1500 ppm, and in a solution containing the Pd-precursor compound does not exceed 600 ppm, more preferably 300 ppm and most preferably 100 ppm.

Particularly preferably in the method according to the invention, non-oxidizing atmospheres are used which contain no or almost no oxygen or other gases having an oxidizing effect. The non-oxidizing atmosphere can be an inert gas atmosphere or a reducing atmosphere or a mixture of both gas variants.

In a variant of the method according to the invention, the reduction is carried out in an inert gas atmosphere. In this case the counterions of the metal ion in the metal-containing precursor compound have a reducing effect or the metal complexes disproportionate under the selected process conditions to the oxidation state zero.

In another variant of the method according to the invention the temperature treatment can be used directly in a precursor compound $Pd(NH_3)_4(OH)_2$ and as Au-containing precursor compound $NaAuO_2$ or $KAuO_2$, particularly preferably $KAuO_2$.

After the steps of spraying on the precursor compounds and before step (d) the support body is preferably subjected to a drying step. The drying step preferably takes place in the same way as further above in connection with the optional drying steps between steps (b) and (c) or (c1).

As already stated step (d) is preferably carried out in a non-oxidizing atmosphere to reduce the metal components of the precursor compound to the elemental metals.

The temperature treatment in a non-oxidizing atmosphere is preferably in a temperature range of from 60° C. to 500° C.

By a non-oxidizing atmosphere is meant in the present invention an atmosphere which is inert or has a reducing effect. In this case, the precursor compounds are decomposed at the same time and the metal components are reduced to the elemental metals. This means that decomposition and reduction are carried out simultaneously at the same temperature in the reducing atmosphere. In this case, the temperature treatment preferably takes place in a range above or equal to 40° C. to 400° C., more preferably 50° C. to 300° C., even more preferably 60° C. to 250° C. and most preferably in the range of from 70° C. to 180° C.

In yet another variant of the method according to the invention, the temperature treatment is preferably carried out such that there is a change from an inert gas atmosphere to a reducing atmosphere during the temperature treatment. This method thus saves energy and costs. This is possible in particular because starting materials are used to start with which do not have such high decomposition temperatures as, for example, chlorine-containing compounds.

The precursor compounds are first decomposed at their decomposition temperature in an inert gas atmosphere and then the metal components are reduced to the elemental metals by the change to a reducing atmosphere. The temperature during the decomposition under inert gas preferably lies in the range of from 200 to 500° C., more preferably 250 to 450° C. and most preferably above 300° C. The temperature during the subsequent reduction then preferably lies in the range above or equal to 40° C. to 400° C., more preferably 40° C. to 300° C., even more preferably 45° C. to 250° C. and most preferably in the range of from 50° C. to 180° C.

All three method variants have the advantage that a precalcining or intermediate calcining in a further upstream or intermediate step in another unit can be dispensed with. Thus, the method according to the invention is preferably carried out by dispensing with laborious cooling to below the decomposition temperature and heating to above the decomposition temperature.

According to the invention, it is particularly preferred that the change from an inert gas atmosphere to a reducing atmosphere is carried out such that the temperature during the change does not fall below the temperature desired for the reduction.

$N_2$, He, Ne, Ar or mixtures thereof for example are used as inert gas. $N_2$ is particularly preferably used.

The component with reducing action in the reducing atmosphere is normally to be selected depending on the nature of the metal components to be reduced, but preferably selected from the group of gases or vaporizable liquids consisting of ethylene, hydrogen, CO, $NH_3$, formaldehyde, methanol, formic acid and hydrocarbons, or is a mixture of two or more of the above-named gases/liquids. The reducing atmosphere particularly preferably comprises hydrogen as reducing component. It is preferred in particular if the reducing atmosphere is formed by forming gas, a mixture of $N_2$ and $H_2$. The hydrogen content is in the range of from 1 vol.-% to 15 vol.-%. The method according to the invention is carried out for example with hydrogen (4-5 vol.-%) in nitrogen as process gas at a temperature in the range of from 60° C. to 500° C. over a period of for example from 1 to 5 hours.

The change named in the second method alternative from inert gas to a reducing atmosphere preferably takes place by feeding one of the named reducing components into an inert gas atmosphere. Hydrogen gas is preferably fed in. The feeding of a gas with a reducing action to the inert gas has the advantage that the temperature does not fall substantially, or not down to or below the lower limit of at least 60° C. desired for the reduction, with the result that there is no need for another cost- and energy-intensive heating due to a corresponding total atmosphere exchange.

In a particularly preferred embodiment, the support body containing the precursor compounds is not exposed to a temperature above or equal to 300° C. in an oxidizing atmosphere before the temperature treatment. In this way, it is guaranteed that the support body with the precursor compounds applied to it is subjected to the temperature treatment, as are the precursor compounds. In other words: a cost-intensive precalcining of the impregnated support body to the metal oxides can be dispensed with. However, it is also possible according to the invention that an intermediate calcining to oxides is carried out.

The shell catalyst produced with the method according to the invention preferably contains an overall proportion of Au in the range of from 0.1 to 1.0 wt-%, more preferably 0.2 to 0.9 wt-%, even more preferably 0.25 to 0.8 wt-% and most preferably in the range of from 0.3 to 0.7 wt-% relative to the total weight of the shell catalyst.

The shell catalyst produced with the method according to the invention preferably contains an overall proportion of Pd in the range of from 0.6 to 2.0 wt-%, more preferably 0.8 to 1.7 wt-%, even more preferably 0.9 to 1.6 wt-% and most preferably in the range of from 1.0 to 1.5 wt-% relative to the total weight of the shell catalyst.

After the reduction of the metal components of the precursor compounds to the elemental metals, in the method according to the invention the promoter KOAc is preferably applied to the subsequently gold-plated support by impregnating the obtained catalyst precursor with an aqueous KOAc solution (preferably aqueous solution) according to the pore-filling method (incipient wetness) at room temperature and typically left to stand for approximately one hour before drying is initiated. The potassium loading preferably lies in the range of from 2 to 3.5 wt-%, more preferably 2.2 to 3.0 wt-% and most preferably 2.5 to 2.7 wt-% relative to the total weight of the dry catalyst. After the application of the KOAc solution a final drying in the range of from 70-120° C., more preferably 80-110° C. and most preferably 90-100° C. can take place in air, lean air or inert gas.

A further subject of the present invention is also a shell catalyst which can be obtained using the method according to the invention. The shell catalyst according to the invention differs from conventional shell catalysts for the synthesis of vinyl acetate and/or allyl acetate in that it exhibits a significantly higher selectivity and activity in the synthesis of vinyl acetate and/or allyl acetate. The structural differences clearly present in respect of the better selectivity and activity of the shell catalyst according to the invention compared with conventional catalysts cannot be expressed in physical values at the time of the application. The shell catalyst according to the invention can therefore only be distinguished from conventional catalysts by the manner of its production and the established increased selectivity and activity.

Another embodiment relates to the use of a shell catalyst produced using a method according to the invention, oxyacetylation of olefins, in particular for producing allyl acetate or vinyl acetate. In other words the present invention also relates to a method for the oxyacetylation of olefins in which acetic acid, an olefin and oxygen or oxygen-containing gases are passed over the catalyst according to the invention. Olefin is here preferably ethylene or propylene. The method generally takes place by passing acetic acid, olefin and oxygen or oxygen-containing gases over the catalyst according to the invention at temperatures of 100-200° C., preferably 120-200° C., and at pressures of 1-25 bar, preferably 1-20 bar, wherein non-reacted educts can be recycled. Expediently, the oxygen concentration is kept below 10 vol.-%. Under certain circumstances, however, a dilution with inert gases such as nitrogen or carbon dioxide is also advantageous. Carbon dioxide is particularly suitable for dilution, as it is formed in small quantities during the vinyl-acetate and/or allyl-acetate synthesis and accumulates in the recycle gas. The formed vinyl acetate/allyl acetate is isolated with the help of suitable methods which are described for example in U.S. Pat. No. 5,066,365 A.

The invention is described in more detail below using a FIGURE and embodiment examples without these being understood as limiting:

FIGURE:

FIG. 1: FIG. 1 shows the VAM selectivities calculated from the measured VAM and $CO_2$ peaks as a function of the $O_2$ conversion using 3 different shell catalysts during the catalytic synthesis of VAM.

EXAMPLES

The percentages relating to the solutions containing the precursor compounds are atomic wt-% of the respective metal relative to the total weight of the solution.

Comparison Example

Catalyst 1

100 g of the support "KA-Zr-14" (KA-160 support doped with 14% $ZrO_2$ from Süd-Chemie) is coated with an aqueous mixed solution of $Pd(NH_3)_4(OH)_2$ and $KAuO_2$ (produced by mixing 27.79 g of a 4.70% Pd solution+12.09 g of a 3.60% Au solution+50 ml of water) in an Innojet IAC025 coater at 70° C. (spraying rate 80%, i.e. 4 g of solution was applied per minute per 100 g of support), then dried at 90° C. for 40 minutes in a fluidized bed dryer and reduced at 150° C. for 4 hours with forming gas. After the reduction a 2-molar KOAc solution is impregnated using the "incipient wetness principle", the impregnation time is one hour. This is again followed by drying in a fluidized bed dryer at 90° C. for 40 minutes. The LOI-free (LOI: loss on ignition) metal contents of the finished catalyst determined by chemical elemental analysis are 1-15% Pd+0.41% Au.

Comparison Example 2

Catalyst 2

100 g of the support "KA-Zr-14" (KA-160 support doped with 14% $ZrO_2$ from Std-Chemie) is coated with an aqueous solution of 27.79 g $Pd(NH_3)_4(OH)_2$ (produced by mixing 27.79 g of a 4.70% Pd solution+50 ml of water) (4.70%) in an Innojet IAC025 coater at 70° C. (spraying rate 80%, i.e. 4 g of solution was applied per minute per 100 g of support) and then coated with 12.09 g of $KAuO_2$ (produced by mixing 12.09 g of a 3.60% Au solution+50 ml of water) in an Innojet IAC025 coater at 70° C. (spraying rate 80%, i.e. 4 g of solution was applied per minute per 100 g of support), dried at 90° C. for 40 minutes in a fluidized bed dryer and reduced at 150° C. for 4 hours with forming gas. After the reduction a 2-molar KOAc solution is impregnated using the "incipient wetness" principle. The impregnation time is one hour. This is again followed by drying in a fluidized bed dryer at 90° C. for 40 minutes. The LOI-free metal contents of the finished catalyst determined by chemical elemental analysis are 1.16% Pd+0.41% Au

Example 1

Catalyst 3

100 g of the support "KA-Zr-14" (KA-160 support doped with 14% $ZrO_2$ from Süd-Chemie) is coated with an aqueous solution of 12.09 g of $KAuO_2$ (produced by mixing 12.09 g of a 3.60% Au solution+50 ml of water) in an Innojet IAC025 coater at 70° C. (spraying rate 80%, i.e. 4 g of solution was applied per minute per 100 g of support) and then coated with 27.79 g of $Pd(NH_3)_4(OH)_2$ (produced by mixing 27.79 g of a 4.70% Pd solution+50 ml of water) in an Innojet IAC025 coater at 70° C. (spraying rate 80%, i.e. 4 g of solution was applied per minute per 100 g of support), dried at 90° C. for 40 minutes in a fluidized bed dryer and reduced at 150° C. for 4 hours with forming gas. After the reduction a 2-molar KOAc solution is impregnated using the "incipient wetness" principle. The impregnation time is one hour. This is again followed by drying in a fluidized bed dryer at 90° C. for 40 minutes. The LOI-free metal contents of the finished catalyst determined by chemical elemental analysis are 1.17% Pd+0.41% Au.

Example 2

Catalyst 4

100 g of the support "KA-Zr-14" (KA-160 support doped with 14% $ZrO_2$ from Süd-Chemie) is coated with an aqueous solution of 3.02 g of $KAuO_2$ (produced by mixing 3.02 g of a 3.60% Au solution+50 ml of water) in a coating drum, (DF-LDP-3 coating pan from D&F Drouven GmbH, see also for example DE 10 2005 061382 A1) at 50° C. (spraying rate 80%, i.e. 4 g of solution was applied per minute per 100 g of support) and then coated with a mixed solution of 27.79 g of $Pd(NH_3)_4(OH)_2$ and 9.07 g of $KAuO_2$ (produced by mixing 27.79 g of a 4.70% Pd solution+9.07 g of a 3.60% Au solution+50 ml of water) in a coating drum at 50° C. (spraying rate 80%, i.e. 4 g of solution was applied per minute per 100 g of support), dried at 90° C. for 40 minutes in a fluidized bed dryer and reduced at 150° C. for 4 hours with forming gas. After the reduction a 2-molar KOAc solution is impregnated using the "incipient wetness" principle, the impregnation time is one hour. This is again followed by drying in a fluidized bed dryer at 90° C. for 40 minutes. The LOI-free metal contents of the finished catalyst determined by chemical elemental analysis are 1.19% Pd+0.42% Au.

Example 3

Test Results of catalysts 1 to 3 in respect of their selectivity during the synthesis of vinyl acetate monomer:

For this, acetic acid, ethylene and oxygen were each passed over the catalysts 1 to 3 at a temperature of 140° C./12 h→143° C./12 h→146° C./12 h (these are the respective reaction temperatures that apply in turn during the automated execution of the screening protocol, i.e. measurement is carried out for 12 h at 140° C., then for 12 h at 143° C., and then for 12 h at 146° C. reactor temperature) and a pressure of 6.5 bar. The concentrations of the components used were: 40.2% ethylene, 6.3% $O_2$, 0.6% $CO_2$, 9.6% methane, 12.68% acetic acid, remainder $N_2$.

FIG. 1 and Table 1 below show the test results for catalysts 1 to 3. Under comparable process conditions, catalyst 4 exhibits a selectivity that lies between the selectivity of catalysts 1 and 2 and the selectivity of catalyst 3.

TABLE 1

| Catalyst 1 | | Catalyst 2 | | Catalyst 3 | |
|---|---|---|---|---|---|
| Selectivity calculated from VAM and CO2 peaks [%] | O2 conversion [%] | Selectivity calculated from VAM and CO2 peaks [%] | O2 conversion [%] | Selectivity calculated from VAM and CO2 peaks [%] | O2 conversion [%] |
| 94.98 | 38.88 | 95.06 | 40.73 | 94.29 | 51.86 |
| 94.92 | 38.92 | 95.07 | 40.66 | 94.26 | 51.88 |
| 94.92 | 38.91 | 95.1 | 40.75 | 94.3 | 51.84 |
| 94.88 | 38.95 | 95.04 | 40.46 | 94.28 | 52.15 |
| 94.92 | 39.64 | 95.02 | 40.47 | 94.27 | 52.28 |
| 94.55 | 42.71 | 94.7 | 44.16 | 93.83 | 56.68 |
| 94.58 | 42.9 | 94.65 | 43.95 | 93.89 | 56.95 |
| 94.58 | 43.16 | 94.74 | 44.21 | 93.93 | 56.86 |
| 94.63 | 42.98 | 94.77 | 43.88 | 93.98 | 56.99 |
| 94.6 | 42.67 | 94.81 | 43.87 | 93.92 | 56.86 |
| 94.64 | 42.94 | 94.82 | 43.97 | 93.92 | 56.91 |
| 94.68 | 43.01 | 94.85 | 43.7 | 93.46 | 60.73 |
| 94.28 | 46.29 | 94.47 | 47.26 | 93.51 | 61.02 |
| 94.31 | 46.6 | 94.41 | 46.92 | 93.56 | 61.03 |
| 94.33 | 46.51 | 94.51 | 47.02 | 93.54 | 60.94 |
| 94.32 | 46.3 | 94.49 | 46.87 | 93.56 | 60.9 |
| 94.27 | 46.25 | 94.49 | 46.68 | 93.56 | 61.15 |
| 94.31 | 46.02 | 94.44 | 46.24 | 93.55 | 60.98 |
| 94.29 | 46.42 | 94 | 49.92 | 93.01 | 64.82 |
| 93.75 | 49.91 | 94.01 | 50.08 | 92.92 | 65.06 |
| 93.77 | 49.82 | 93.95 | 49.89 | 92.96 | 64.86 |
| 93.69 | 49.95 | 93.98 | 49.88 | 92.97 | 64.77 |
| 93.96 | 49.66 | 94.11 | 49.53 | 93.11 | 64.67 |
| 93.84 | 49.37 | 94.13 | 49.6 | 93.13 | 64.61 |
| 93.89 | 49.66 | 94.14 | 49.49 | 93.10 | 64.49 |
| 94.73 | 42.76 | 94.95 | 42.62 | 94.12 | 57.3 |
| 94.84 | 42.34 | 94.97 | 42.44 | 94.14 | 57.02 |
| 94.73 | 42.15 | 94.95 | 42.22 | 94.16 | 56.78 |
| 94.73 | 41.76 | 94.92 | 42.17 | 94.16 | 56.62 |
| 94.76 | 41.84 | 94.99 | 42.1 | | |

The invention claimed is:

1. Method for producing a shell catalyst, comprising the steps of:
    (a) subjecting a packed bed of a catalyst support body to a circulating movement;
    (b) bringing an atomized aqueous solution containing an Au-containing precursor compound into contact with the packed bed of the catalyst support body subjected to the circulating movement by spraying on of the solution;
    (c) bringing an atomized aqueous solution containing a Pd-containing precursor compound with the catalyst support body produced after step (b); and
    (d) reducing the metal components of the precursor compounds to elemental metals by subjecting the catalyst support body obtained in step (c) to a temperature treatment in a non-oxidizing atmosphere.

2. Method according to claim 1, wherein, during the bringing into contact in step (c), the solution is sprayed onto a packed bed of the catalyst support body subjected to a circulating movement.

3. Method according to claim 1, wherein the temperature treatment is carried out within a range of from 60° C. to 500° C.

4. Method according to claim 2, wherein the circulating movement of the catalyst support bodies is carried out with a process gas.

5. Method according to claim 2, wherein the circulating movement of the catalyst support bodies takes place in a fluid bed or a fluidized bed.

6. Method according to claim 1, wherein the ratio of the weight of the solution sprayed on in step (b) or (c) to the weight of the packed bed of the support body lies in the range of from 0.005 to 0.1.

7. Method according to claim 1, wherein in step (c) an Au-containing precursor compound is applied to the catalyst support body.

8. Method according to claim 1, wherein, between steps (c) and (d), an Au-containing precursor compound is applied in a step (c1) to the catalyst support body obtained in step (c).

9. Method according to claim 1, wherein the shell catalyst contains a proportion of Au in the range of from 0.1 to 1.0 wt-% relative to the total weight of the shell catalyst.

10. Method according to claim 1, wherein the shell catalyst contains a proportion of Pd in the range of from 0.6 to 2.0 wt-% relative to the total weight of the shell catalyst.

11. Method according to claim 1, wherein the Pd-containing precursor compound is a compound selected from the group consisting of a nitrate compound, nitrite compound, acetate compound, tetraammine compound, diammine compound, hydrogen carbonate compound, hydroxidic metallate compounds and mixtures thereof.

12. Method according to claim 1, wherein the Au-containing precursor compound is selected from the group consisting of an acetate compound, nitrite compound, nitrate compound, hydroxidic metallate compound and mixtures thereof.

13. Method according to claim 1, wherein the Au-containing precursor compound is selected from the group consisting of $NaAuO_2$, $KAuO_2$, $LiAuO_2$, $RbAuO_2$ and mixtures thereof.

14. Method according to claim 1, wherein the catalyst support body after step (b) contains a proportion of Au in the range of from 0.1 to 1.0 wt-% relative to the total weight of the catalyst support body.

15. Method according to claim 1, wherein the catalyst support body after step (c) contains a proportion of Au in the range of from 0.6 to 2.0 wt-% relative to the total weight of the catalyst support body.

16. Method according to claim 1, wherein the non-oxidizing atmosphere contains a reducing agent.

17. Method according to claim 16, wherein the reducing agent is hydrogen.

18. Shell catalyst made by a process comprising the steps of:
    (a) subjecting a packed bed of a catalyst support body to a circulating movement;
    (b) bringing an atomized aqueous solution containing an Au-containing precursor compound into contact with the packed bed of the catalyst support body subjected to the circulating movement by spraying on of the solution;
    (c) bringing an atomized aqueous solution containing a Pd-containing precursor compound with the catalyst support body produced after step (b); and
    (d) reducing the metal components of the precursor compounds to elemental metals by subjecting the catalyst support body obtained in step (c) to a temperature treatment in a non-oxidizing atmosphere.

19. A shell catalyst according to claim 18 for the oxyacetylation of olefins.

* * * * *